US00PP09172P

United States Patent [19]

Christensen

[11] Patent Number: Plant 9,172

[45] Date of Patent: Jun. 20, 1995

[54] FLORIBUNDA ROSE PLANT NAMED 'JACSEDI'

[75] Inventor: Jack E. Christensen, Ontario, Calif.

[73] Assignee: Bear Creek Gardens, Inc., Medford, Oreg.

[21] Appl. No.: 281,253

[22] Filed: Jul. 26, 1994

[51] Int. Cl.[6] ..... A01H 5/00

[52] U.S. Cl. ..... Plt./27

[58] Field of Search ..... Plt. 22, 26, 27, 28

[56] References Cited

U.S. PATENT DOCUMENTS

P.P. 3,846 3/1976 Kordes ..... Plt./27

P.P. 8,183 3/1993 Carruth ..... Plt./27

*Primary Examiner*—Howard J. Locker

*Attorney, Agent, or Firm*—Klarquist Sparkman Campbell Leigh & Whinston

[57] ABSTRACT

A floribunda rose plant having upright, vigorous growth; fragrant, deep lavender flowers; healthy, dark green, glossy foliage; and floribunda growth habit.

1 Drawing Sheet

1

The present invenion relates to a new and distinct variety of rose plant of the floribunda class which was originated by me by crossing an unnamed seedling with the variety TINdilly (U.S. Plant Pat. No. 6,141).

The primary objective of this breeding was to produce a new rose variety having the vigorous, upright growth habit and healthy foliage of the unnamed seedling female combined with the fragrant lavender flowers of the male parent. Because both parents were miniatures with hybrid teas in their background, another objective was to produce either a miniature or a floribunda seedling. The seedling of this application was a floribunda plant in which the other objectives were substantially achieved, along with other desirable improvements, as evidenced by the following unique combination of characteristics that are outstanding in the new variety and that distinguish it from its parents, as well as from all other varieties of which I am aware:

1. Strong, upright growth;
2. Healthy, glossy, dark green foliage;
3. A deep lavender flower color;
4. Fragrance; and
5. A floribunda growth habit.

Asexual reproduction of this new variety by budding, as performed at Wasco, shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage

*Seed parent.*—An unnamed seedling.

*Pollen parent.*—TINdilly (U.S. Plant Pat. No. 6,141).

Classification:

*Botanical.*—*Rosa hybrida.*

*Commercial.*—Floribunda.

2

FLOWER

Observations made from specimens grown in a garden environment at Somis, Calif., in March through November, 1993.

Blooming habit: Recurrent.

Bud:

*Size.*—1¼ inches long when the petals start to unfurl.

*Form.*—The bud form is long, pointed ovoid.

*Color.*—When sepals first divide, bud color is Greyed-Purple Group 187D. When half blown, the upper and lower sides of the petals are Greyed-Purple Group 186B.

*Sepals.*—Color Green Group 138B. Surface texture: Covered in fine hairs. There are three normally-to-heavily appendaged sepals. There are two unappendaged sepals with hairy edges.

*Receptacle.*—Color: Green Group 137D. Shape: Apple. Size: Medium (⅝ inch×⅝ inch). Surface: Smooth.

*Peduncle.*—Length: Medium (2½ inches). Surface: Smooth. Color: Medium green and bronzy. Strength: Stiff, erect.

Bloom:

*Size.*—Medium. Average open size is 3½ inches.

Borne.—Singly and several together, in flat clusters of 3 to 5 flowers.

*Stems.*—Short. Average length is about 10 to 14 inches.

*Form.*—When first open: High centered. Permanance: Flattens, outer petals curl back.

*Petalage.*—Number of petals under normal conditions: 30.

*Color.*—The upper and reverse sides of the petals are Greyed-Purple Group 186B. The base of each petal has a small (¼ inch×¼ inch) white half-moon at the point of attachment. The major color on the upper side is Greyed-Purple Group 168B.

*Variegations.*—None.

*Discoloration.*—No change in the general tonality at the end of the first day or at the end of the third day.

*Fragrance.*—Strong.

Petals:

*Texture.*—Thick, leathery.

*Shape.*—Round.

*Form.*—Tips slightly recurved.

*Arrangement.*—Imbricated, with no petaloids in the center.

*Persistence.*—Hang on and dry.

*Lastingness.*—On the plant: Long (6 to 7 days). As a cut flower: Long (7 to 8 days).

Reproductive parts:

*Anthers.*—Size: Medium. Quantity: many. Color: Yellow. Arrangement: Regular around styles.

*Filaments.*—Color: White.

*Pollen.*—Color: Lemon yellow.

*Styles.*—Color: White

*Stigmas.*—Color: Greenish white.

Form: Bush.

Growth: Vigorous, upright, branching.

Foliage:

*Number of leaflets on normal mid*-stem leaves.—5 or 7.

*Size.*—Large (5 inches×4 inches).

*Quantity.*—Abundant.

*Color.*—New foliage: Greyed-Purple Group 183A. Old foliage: Green Group 139A.

Leaflets

*Shape.*—Pointed oval.

*Texture.*—Upper side: leathery, glossy.

*Edge.*—Serrated.

*Serration.*—Single, small.

*Petiole rachis.*—Color: Green with reddish blush, especially at the point of leaflet attachment.

*Petiole underside.*—Smooth, with prickles.

*Stipules.*—Short, bearded.

*Disease resistance.*—Resistant to mildew and rust under normal growing conditions at Somis, Calif.

Wood:

*New wood.*—Color: Light green, with reddish cast. Bark: Smooth.

*Old wood.*—Color: Green. Bark: Smooth.

Prickles:

*Quantity.*—On main canes from base: Ordinary. On laterals from main canes: Ordinary.

*Form.*—Short, hooked downward.

*Color when young.*—Red.

Small prickles:

*Quantity.*—On main stalks: None. On laterals: None.

I claim:

1. A new and distinct variety of rose plant of the floribunda class, substantially as herein shown and described, characterized particularly as to novelty by the unique combination of its upright, vigorous growth; fragrant, deep lavender flowers; healthy, dark green, glossy foliage; and floribunda growth habit.

* * * * *

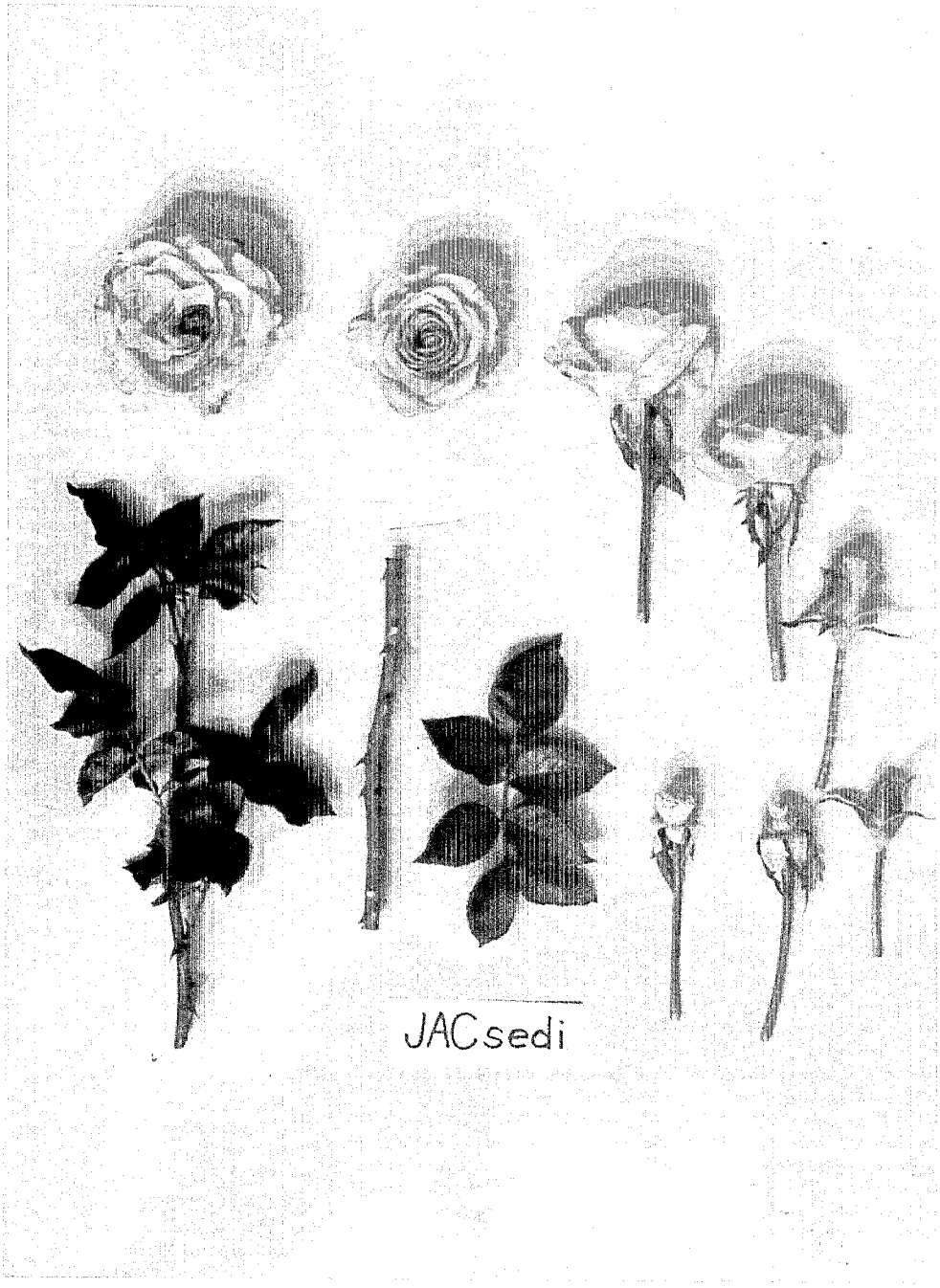
JACsedi